US010702718B2

(12) United States Patent
Yu et al.

(10) Patent No.: US 10,702,718 B2
(45) Date of Patent: Jul. 7, 2020

(54) INTEGRATED MULTI-MODAL PHANTOM FOR COMBINED DOSIMETRY AND POSITIONING VERIFICATION

(71) Applicant: The Board of Trustees of the Leland Stanford Junior University, Stanford, CA (US)

(72) Inventors: Shu-Jung Yu, Stanford, CA (US); Tyler Fowler, Roseburg, OR (US); Lawrie Skinner, Redwiid, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 14 days.

(21) Appl. No.: 16/280,738

(22) Filed: Feb. 20, 2019

(65) Prior Publication Data

US 2019/0175951 A1  Jun. 13, 2019

Related U.S. Application Data

(63) Continuation-in-part of application No. 16/195,009, filed on Nov. 19, 2018, now abandoned.

(60) Provisional application No. 62/588,633, filed on Nov. 20, 2017.

(51) Int. Cl.
*A61N 5/10* (2006.01)
*A61B 6/00* (2006.01)

(52) U.S. Cl.
CPC ............ *A61N 5/1075* (2013.01); *A61B 6/583* (2013.01); *A61N 5/1049* (2013.01); *A61N 5/1071* (2013.01); *A61N 2005/1076* (2013.01)

(58) Field of Classification Search
CPC .. A61N 5/1075; A61N 5/1049; A61N 5/1071; A61N 2005/1076; A61B 6/583
USPC ....................................................... 250/252.1
See application file for complete search history.

(56) References Cited

U.S. PATENT DOCUMENTS

| | | | |
|---|---|---|---|
| 6,318,146 B1 * | 11/2001 | Madsen | A61B 8/08 324/308 |
| 6,594,336 B2 * | 7/2003 | Nishizawa | A61B 6/583 250/367 |
| 9,643,029 B2 * | 5/2017 | Scheib | A61N 5/1049 |
| 2015/0085993 A1 * | 3/2015 | Scheib | A61N 5/1049 378/207 |
| 2017/0080254 A1 * | 3/2017 | Scheib | A61N 5/1071 |

(Continued)

*Primary Examiner* — Taeho Jo
(74) *Attorney, Agent, or Firm* — Lumen Patent Firm (57) ABSTRACT

An integrated quality assurance (QA phantom) for radiotherapy is provided that includes a cubic housing having a raised topology feature and laser alignment marks on an exterior surface of the cubic housing that is adjacent and perpendicular to the anterior surface, an extendable leg disposed on a edge of the housing, where the housing rests on a treatment couch surface when the leg is in the retracted state, and the housing rests on the treatment couch in a tilted position when the leg is in the deployed state, and a rotational stage disposed within the housing that includes at least one radiofrequency beacon, where the rotational stage includes a rotation actuator that is external to the cubic housing, where the invention enables verification of radiotherapy an optical surface monitoring system, a rotational verification of the radiotherapy optical surface monitoring system, and verification of a radiofrequency beacon tracking system.

10 Claims, 6 Drawing Sheets

(56) References Cited

U.S. PATENT DOCUMENTS

2017/0165505 A1\* 6/2017 Arican ................. A61N 5/1075
2017/0347987 A1\* 12/2017 Hong ..................... A61B 6/583

\* cited by examiner

INTEGRATED MULTI-MODAL PHANTOM FOR COMBINED DOSIMETRY AND POSITIONING VERIFICATION

CROSS-REFERENCE TO RELATED APPLICATIONS

This application is a continuation-in-part of U.S. patent application Ser. No. 16/195,009 filed Nov. 19, 2018, which is incorporated herein by reference. U.S. patent application Ser. No. 16/195,009 filed Nov. 19, 2018 claims priority from U.S. Provisional Patent Application 62/588,633 filed Nov. 20, 2017, which is incorporated herein by reference.

FIELD OF THE INVENTION

The present invention relates generally to radiotherapy quality assurance. More particularly, the invention relates to a single integrated phantom that can be used for quality assurance for multiple radiotherapy localization/positioning systems and the function of dosimetry measurement.

BACKGROUND OF THE INVENTION

The two quality assurance (QA) objectives of positioning and dosimetric accuracy currently require multiple phantom setups for radiation therapy before patient get treated or the periodic QA to ensure performance of the system. Various localization and positioning systems with the use of radiographic or non-radiographic methods have been developed to improve the accuracy of radiation treatment. Dose measurement was usually performed independently. However, there is no single integrated phantom that can be used for QA for all systems, as well as dose measurements. Each QA procedure requires its own phantom and is independent from each other, so the deviation between each system is unavailable.

With escalated doses and decreased margin for radiation therapy treatment, a positioning system with higher accuracy is essential, as well as dose measurements. In order to deliver the dose precisely, several localization techniques have been developed for positioning the patients so the treatment can be delivered with precision and efficiency. Those techniques are used before and/or during the treatment to setup and monitor patient position. There are two categories, which are radiographic and non-radiographic radiotherapy localization and positioning systems. For radiographic system, it includes kV/MV portal images, cone beam computed tomography (CBCT) and Winston-Lutz test to verify the radiation isocenter. For non-radiographic system, it includes optical surface monitoring system, a 3D imaging technology that provides high resolution and accurate 3D surface data referenced to the treatment isocenter, and radiofrequency (RF) beacon tracking system, a tracking device using RF waves to localize the target. Each localization system requires periodic measurements of specified parameters to ensure that hardware and software functions safely and reliably perform as expected. Each quality assurance (QA) needs its own procedure and phantom and the deviation between each system is unavailable. It is time consuming to setup the QA phantom and to perform the QA procedure for each system. The reproducibility of the phantom setup is dependent the QA physicist. The space to store the QA phantoms can grow very quickly with the number of phantoms required for the QA. Moreover, the QA phantoms for RF tracking and optical surface monitoring systems are provided by the manufacture, which leads to self-QA and it is not an independent check from the vendor. There are few phantoms that were developed for each technique but none of them can do the QA for all systems.

What is needed is a method and device that combines the QA tests into a single phantom, to have an independent QA method from the vendor, to reduce the number of phantoms required for QA, to reduce the time required of the medical physicist to perform these QA tasks, and to increase the reproducibility of phantom placement to evaluate the deviation of isocenter between the individual systems.

SUMMARY OF THE INVENTION

To address the needs in the art, an integrated localization and dosimetry phantom quality assurance (QA) system for radiotherapy that includes a cubic housing having a raised topology feature on an exterior surface of the cubic housing, and at least one laser alignment mark on an exterior surface of the cubic housing that is adjacent and perpendicular to the anterior surface, at least one extendable leg disposed on a edge of the cubic housing, where the at least one extendable leg includes a retracted state and an extended state, where the cubic housing rests on a treatment couch surface when the at least one extendable leg is in the retracted state, where when in the extended state the at least one extendable leg is disposed downward from the edge of the cubic housing, where the cubic housing rests on the treatment couch surface in a tilted position when the at least one extendable leg is in the deployed state, and a rotational stage disposed within the cubic housing, where the rotational stage includes at least one radiofrequency beacon, where the rotational stage includes a rotation actuator that is external to the cubic housing, where the rotational stage enables verification of a radiofrequency beacon tracking system, where the raised feature enables verification of a radiotherapy optical surface monitoring system, where the at least one tilt leg enables a rotational verification of the radiotherapy optical surface monitoring system.

According to one aspect of the invention, the rotational stage includes a drum disposed within a center region inside the cubic housing, where the at least one radiofrequency beacon for the RF tracking system has a distribution of 3 ceramic ball bearings for imaging localization, and a dosimeter for dose measurement. According to one aspect the drum includes an independent insertable isocenter ball bearing, where the drum has at least one dosimeter insert, where the at least one dosimeter insert comprises a holder configured to translate between a first position and a second position, where the first position includes the dosimeter at an isocenter position and the second position includes the ball bearing at the isocenter, where the insert has a two part construction configured for inspecting the ball bearing and the dosimeter placement. The drum severs as the buildup marital for the dose measurement.

According to one aspect of the invention, the raised feature that includes a nonlinear raised feature.

In another aspect of the invention, the at least one laser alignment mark includes a vertical laser alignment mark and a horizontal laser alignment mark.

In a further aspect of the invention, the rotational stage is disposed for rotational verification of radiofrequency beacon tracking, where the at least one radiofrequency beacon is disposed on at least one planar sheet, where the at least one planar sheet is separated from another the at least one planar sheet holding another the at least one beacon, where the separation of the planar sheets is configured for a Winston-Lutz test.

According to yet another aspect of the invention, the rotational stage further includes an isocenter element, where the isocenter element is disposed at an interior isocenter the cubic housing, where the at least one radiofrequency beacon is disposed outside a field of radiation directed at the isocenter element, where the at least one radiofrequency beacon and the isocenter element enable verification of a QA test that can include a kV radiology imaging test, a MV radiology imaging test, cone beam computed tomography (CBCT) test, and a Winston-Lutz radiology test.

In one aspect of the invention, the at least one radiofrequency beacon is disposed outside a radiation field when the beacons will be outside radiation field for Winston-Lutz test.

According to another aspect of the invention, the cubic housing includes a 3D printable material.

In another aspect the invention further includes further comprising an integrated localization and dosimetry phantom positioning bar mount configured to affix to said treatment couch.

BRIEF DESCRIPTION OF THE DRAWINGS

(FIG. 1C) shows a core for radiofrequency beacon tracking system alignment was placed outside the field for Winston-Lutz test, according to the current invention.

DETAILED DESCRIPTION

In this application, a novel phantom was designed and evaluated to integrate QA procedures for two main QA objectives, positioning and dosimetric accuracy, which currently involve multiple phantom setups. To solve these issues of co-alignment, simplify the QA process, and reduce errors, we developed an integrated phantom which allows independent verification of each positioning system and coincidence of each system and with the same setup without moving the phantom the dosimetric function can be performed. This phantom not only allows for eight alignment QA tests to be performed with a single setup (kV, MV, CBCT, RF-tracking, optical surface imaging, Winston-Lutz test, light/radiation field coincidence and lasers), but also a dose measurement.

The current invention provides a single integrated phantom that can be used for quality assurance (QA) for multiple radiotherapy localization and positioning systems, as well as dose measurement. Previously, each QA procedure requires its own phantom and is independent from each other, so the deviation between each system is unavailable.

According to one embodiment, the invention includes a phantom having an internal rotational stage that can be rotated to a predefined angle for testing of the accuracy of the radiofrequency localization system to detect the target rotation while maintaining the precise position of the isocentric bearing. The rotational core can be easily adjusted from outside the phantom with a small handle and set to the predefined angle. This rotational core for the radiofrequency beacon tracking system alignment was designed so beacons were placed outside the radiation field. Therefore, there is no confusion when performing the imaging analysis for Winston-Lutz test. In one embodiment, there are eight internal fiducials for imaging alignment and a 6 mm isocentric bearing for Winston-Lutz test. The phantom can also be tilted to a predefined angle using the extendable legs to test the accuracy of the optical surface mapping localization system to detect the rotation of the object. In another embodiment, externally, the phantom features 1 mm wide grooves to check that laser alignment is within tolerance and aid in adjustment of laser positioning. The surface of the phantom includes the features of a curved surface (or raised letters "S", "A", and "R", for example) and shape to create the unique surface topography for tracking with the optical surface mapping system. The phantom can be scanned using a CT scanner and the physicist can perform the QA with a plan created in their own treatment planning system.

Disclosed herein, according to one embodiment, the integrated phantom was designed in 3D CAD software and 3D printed. The phantom was designed with laser alignment marks, a raised letter "S", or a surface topology on the surface for optical surface monitoring system registration, a core for radiofrequency (RF) beacon tracking system alignment, a plurality of internal fiducials for image alignment, and an isocentric bearing for Winston-Lutz test. At least one tilt leg and rotational stage are provided for rotational verification of optical surface monitoring system and radiofrequency beacon tracking system systems, respectively. The phantom can be scanned using a CT scanner and a QA plan was created. This example phantom was evaluated against to the established QA procedure.

As described herein, the QA result between the proposed phantom and established QA phantoms are, respectively, 1.05±0.20 and 1.14±0.31 mm for RF beacon tracking system and 0.18±0.06 and 0.18±0.05 mm for Winston-Lutz test. The accuracy of rotational verification for optical surface monitoring system and RF beacon tracking system are less than 0.5 degree compared the predefined value. The isocenter deviation of each location system is around 1 mm.

From the beginning the QA phantom was designed to be easy to use, require minimal manipulation after setup, decrease QA time, and include the maximum amount of QA features inside a small footprint. The integrated phantom was designed in SolidWorks 3D CAD software (Dassault Systèmes, Vélizy-Villacoublay, France) and 3D printed using a Ultimaker 2+ printer (Ultimaker B. V., Geldermalsen, Netherlands) with 0.4 mm printing nozzle and 0.1 mm layer resolution and polylactic acid (PLA) material. The reason PLA was chosen for printing material is its abundance, ease of use, and cost effectiveness for rapid prototyping. The phantom was 3D printed in twelve separate parts and assembled afterwards using nylon hardware. The phantom was designed with laser alignment marks for initial phantom setup and a curved to create a feature or a surface topology on the surface for optical surface monitoring system registration. A core for RF beacon tracking system alignment was designed so beacons were placed outside the radiation field. Therefore, there is no confusion when performing the imaging analysis for Winston-Lutz test.

FIGS. 1A-1E show the different views of the integrated phantom. The (FIG. 1A) control levers on the backside and laser alignment marks on at least a topside, (FIGS. 1B-1C) an internal backside view of the phantom controls, (FIG. 1D) an exploded view of the insertable bar for hosting a dosimeter and BB, and (FIG. 1E) a perspective view of the integrated phantom front side. (FIG. 1C) shows a core for radiofrequency beacon tracking system alignment was placed outside the field for Winston-Lutz test, according to the current invention.

The integrated phantom was scanned using a CT scanner (Discovery 710, GE Healthcare) with 1.25 mm slice thickness and 120 kVp. A QA plan was created with the ability to image for positioning purpose, deliver Winston-Lutz test and the dose measurement. The optical surface monitoring system uses 3D point cloud to represent the outline of phantom's body obtained from a video camera-based in-room monitoring system and compares it with a CT-derived surface image as a reference. Therefore, a body contour of integrated QA phantom was created and carefully evaluated in the treatment planning system (Eclipse, Varian, Palo Alto, Calif.) and exported to the optical surface monitoring system on the treatment console. For RF beacon tracking system, the beacons were identified and marked/localized in the treatment planning system and imported into the RF beacon tracking workstation. The individual test for each system was performed and compared to the vendor-provided QA method to evaluate the Phantom. After integrated QA phantom was validated against to vendor's method, an integrated QA procedure was performed to evaluate the deviation of the isocenter position of each location system.

Two-sided paired t-test was used to evaluate the difference of the QA results between the integrated QA phantom and vendor's phantom, and differences with p>0.05 were considered statistically insignificant.

Both vendor's phantom and the integrated QA phantom contain three beacon transponders used to verify the system performance. Beacon transponders were used to identify the changes in calibration. Each phantom was aligned with laser on the couch. Distance (D) between QA phantom isocenter to the calibrated radiofrequency beacon tracking system isocenter was recorded for both phantoms. The isocenter off set was calculated by Eq (1):

$$D=\sqrt{X_{QA}^2+Y_{QA}^2+Z_{AQ}^2} \qquad \text{Eq (1)}$$

where $X_{QA}$, $Y_{QA}$, and $Z_{QA}$ are the distances of the QA isocenter to the calibrated radiofrequency beacon tracking system isocenter in the X, Y, and Z axes, respectively.

Figure 2A:
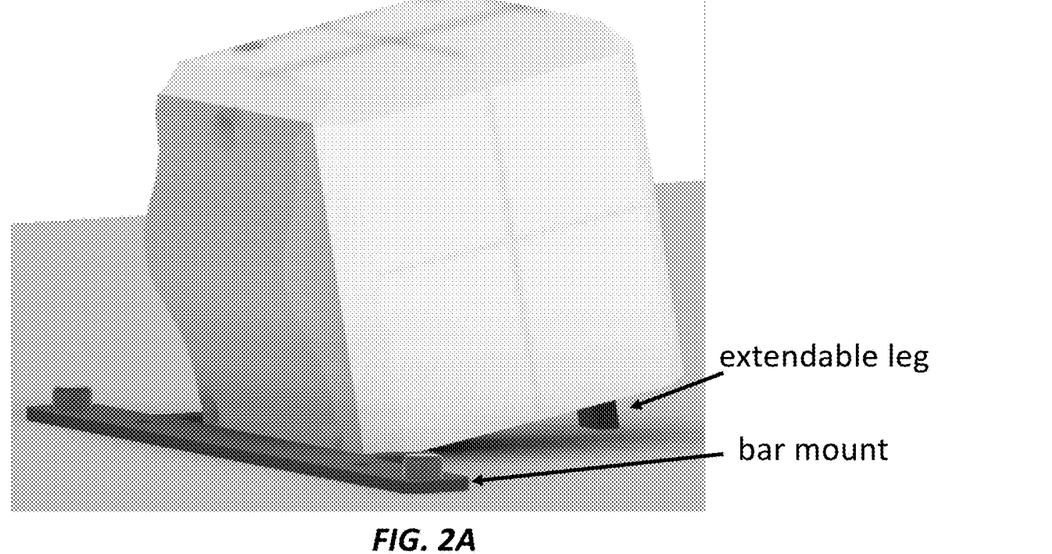
FIGS. 2A-2B show integrated quality assurance phantom featuring (2A) a raised back end resting on the extendable leg, and (2B) the integrated phantom in a level position, according to the current invention. show the accuracy of position and rotational verification for the optical surface monitoring system. This is the only phantom which can do the rotational verification for the optical surface monitoring system, according to the current invention.
Figure 2B:
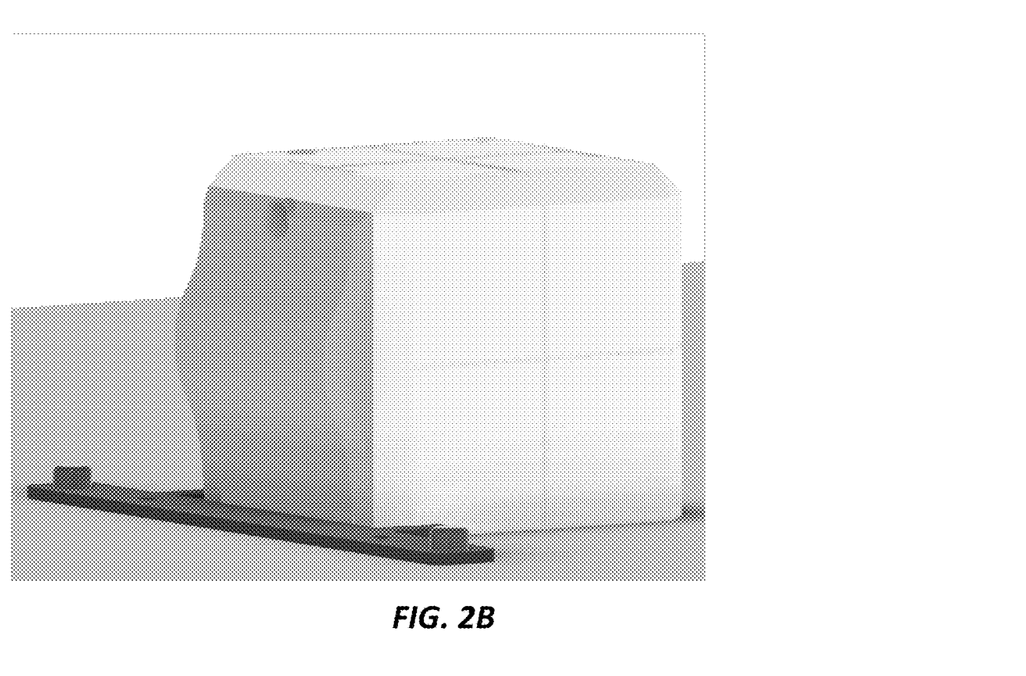

A calibration plate, an optical surface monitoring system QA phantom provided by the vendor, with a printed grid of circles was placed on the couch with the center of the plate aligned to the isocenter. The cameras take images of the plate and process the images to identify the center of each circle registration. This procedure does not provide the distance between QA phantom isocenter to calibrated isocenter so the relative shift between two cameras was recorded. Once the integrated QA phantom was setup with images, the deviation between the DICOM reference surface and the integrated QA phantom surface was recorded. Tilt legs were extended to verify pitch for the optical surface monitoring system. FIGS. 2A-2B show integrated quality assurance phantom featuring (2A) a raised back end resting on the extendable leg, and (2B) the integrated phantom in a level position, according to the current invention. This is to test the accuracy of position and rotational verification for the optical surface monitoring system. This is the only phantom which can do the rotational verification for the optical surface monitoring system, according to the current invention.

Figure 3A:
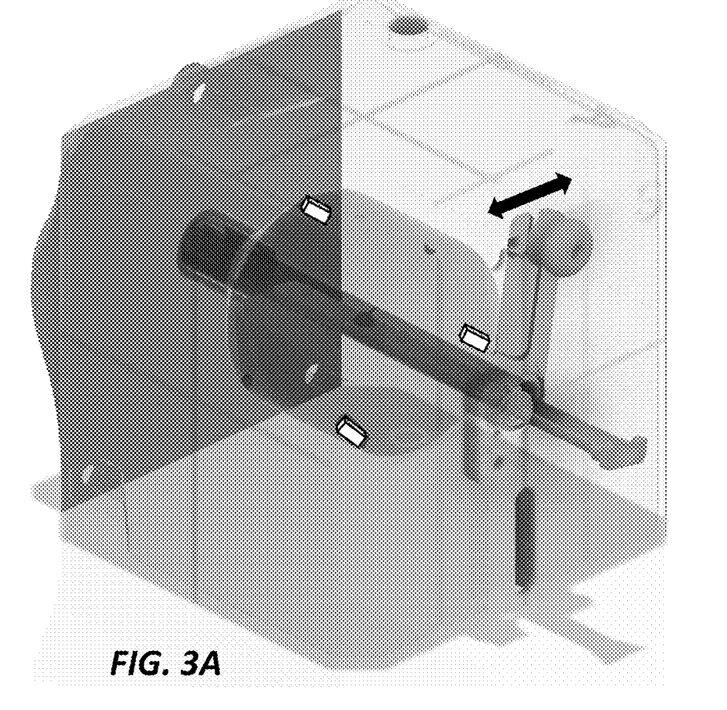
FIGS. 3A-3B show the function of the accuracy of position and rotational verification for RF beacon tracking system. This is the only phantom which can do the rotational verification for RF beacon tracking system, according to the current invention. Switching the rotation knob to the index slot (two stages, left and right) which makes the beacons rotate a predefined angle while the insert stays stationary, according to the current invention.
Figure 3B:
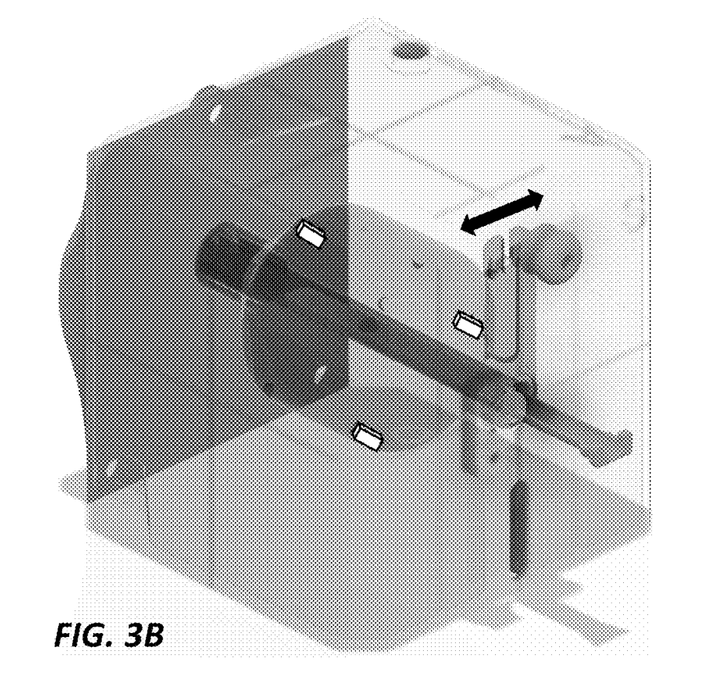

The rotational stage was switched left and right to verify rotation of radiofrequency beacon tracking system. FIGS. 3A-3B show the accuracy of position and rotational verification for RF beacon tracking system. This is the only phantom which can do the rotational verification for RF beacon tracking system, according to the current invention.

Once the integrated QA phantom was setup up by the images, the images of radiation field with the bearing ball at the center were acquired by the electronic portal imaging device (EPID). The gantry angles were 0°, 90°, 180°, and 270°. The couch angles were 0°, 45, 90°, 270° and 315°. The collimator angles were 0°, 90°, and 270°. Same procedure was performed with a Winston-Lutz phantom provided by the vendor. EPID images were analyzed by RIT V6.5.64 software (Radiological Imaging Technology, Colorado Springs, Colo.).

The integrated QA phantom was initially positioned on the treatment couch with laser. A pair kV image and cone beam computed tomography (CBCT) were taken for the fine adjustment. After the phantom was positioned on the couch, the optical surface monitoring system was turned on and the deviation between the DICOM file from treatment planning system and the phantom position on the couch was recorded for the lateral, longitudinal, and vertical directions, as well as the rotation, pitch and roll for couch position at 0°, 45°, 90°, 270°, and 315°. The deviation of isocenters between the image and radiofrequency beacon tracking system were recorded while phantom was at the same location with the radiofrequency beacon tracking station. Winston-Lutz Test was performed and analyzed as described above.

Figure 4A:
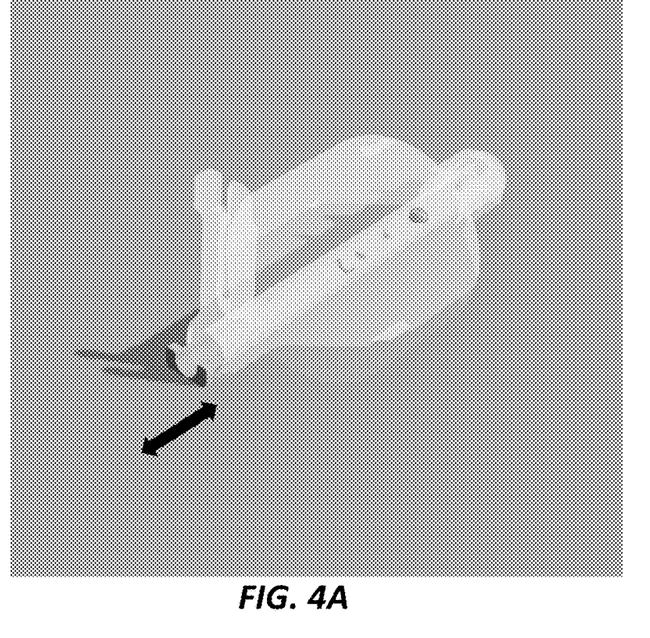
FIGS. 4A-4B show a movable insert which can switch between the dose measurement (4A) and central BB, Winston-Lutz test, (4B) without moving the phantom itself, according to the current invention.

For dose measurements, ten anonymized clinical brain SRS plans were delivered onto the phantom with either 6 MV FFF (n=5) or 10 MV FFF (n=5). These plans were delivered with a Varian Truebeam linac, and the HD MLC. This dose was then compared to three other methods: i) the treatment planning system (TPS) calculations, ii) ion chamber measurements in a solid water phantom, and iii) radiochromic film measurements. A small ionization chamber specifically developed for small field dosimetry measurements Pinpoint 31014 by PTW (PTW Model N31014, Freiburg, Germany) was used in this study. A verification plan was created with the CT image of the phantom. The measured dose was compared to the calculated mean dose in the TPS with the Acuros® XB algorithm (AXB, Varian Medical Systems Inc. Palo Alto, Calif.) and 1 mm calculation grid. The mean dose calculated by TPS was the mean value within a contour located at the ion chamber with radius 1 mm and length 5 mm. The daily output correction factor was applied to correct the daily output variation with field size 10×10 cm, 100 SSD at 1.5 cm and 2.4 depth for 6 MV FFF and 10 MV FFF, respectively. The pinpoint ion chamber was placed beforehand in the insertable bar and the inert bar was pushed to the second position where the ion chamber is located at the isocenter (FIG. 4A). A constant conversion factor was used to derive dose from the ratio of delivered dose under the reference condition to the collected charge. Measurements were made on randomized SRS patient plans for 6 MV FFF and 10 MV FFF. EBT-XD films were scanned 24 h after irradiation with an Epson 10000 XL flatbed scanner (Epson, Nagano, Japan). After warming up the scanner, films were placed at the center of the scanner and scanned in portrait orientation with no color correction. The scanned images were analyzed using radiochromic.com by placing the crosshair over the region of interest (ROI, 2×2 mm). A verification plan was created with 10 cm backscatter and 10 cm buildup solid water. The measured dose was compared to calculated dose exported from the TPS with the Acuros® XB algorithm and 1 mm calculation grid (AXB, Varian Medical Systems Inc. Palo Alto, Calif.). The dose from TPS was exported with 512×512 points without a burn marker. Target sizes ranges from 1.83 cc to 7.51 cc. A daily output variation was measured with 10×10 field size at 1.5 cm and 2.4 cm depth for 6 MV FFF 10 MV FFF, respectively.

For the solid water phantom ion chamber measurements, a verification plan was created with 10 cm backscatter and 10 cm buildup solid water. The same TPS settings, daily output correction, ion chamber, and alignment procedure were used as for the phantom measurements.

The QA result with the use of integrated QA phantom and the QA phantom provided by vendor are 1.12±0.31 and 1.14±0.31 mm (n=10) for RF beacon tracking system, and 0.18±0.06 and 0.18±0.05 mm (n=10) for Winston-Lutz test. The laser alignment agrees within 0.5 mm. The accuracy of rotational verification for optical surface monitoring system and RF beacon tracking system is less than 0.5 degree compared the predefined value. However, for optical surface monitoring system, the vendor provided daily QA procedure only reports the relative shift between two cameras pods that is not the distance between the calibrated isocenter and the phantom isocenter. Therefore, the relative shift between two camera pods, 0.30±0.16 mm (n=10), was reported here. The result of integrated QA phantom is 0.44±0.08 mm (n=10) while the couch is at 0° for optical surface monitoring system. The distance of isocenter between the image isocenter and the phantom for the lateral, longitudinal, and vertical directions, as well as the rotation, pitch and roll are listed in Table 1 for each couch angle (n=10).

The optical surface monitoring system deviation from the image iso will be the same as above since integrated QA phantom was positioned by image procedure. The deviation of isocenter between the image iso and the RF beacon tracking system is 1.02±0.20 mm (n=10).

For dosimetry test, three independent dosimetric measurement techniques were performed. Namely, pinpoint ionchamber chamber measurements in the phantom, pinpoint ion chamber measurements in a solid water block, and radiochromic film measurements in a solid water block. The validation of the dose measurement for the phantom was done by comparing the dose to film which serves as the ground truth in this application. The measurement between phantom and the film measurement agrees within 5% for both 6 MV FFF and 10 MV FFF. The film measurements also agree within 5% for both 6 MV FFF and 10 MV FFF for ion chamber measurement in the solid water which is the standard QA procedure for the patient specific QA in the standard care.

The procedure takes about 20 minutes from setup of the integrated QA phantom to finish the data acquisition. The summary of comparison between integrated QA phantom and the vendor's phantom are listed in Table 2.

For the first time, a phantom was designed to streamline the QA procedure for different localization and positioning systems, as well dose measurement. Currently, an optical surface monitoring system is used for head and neck and brain stereotactic radiosurgery (SRS) treatment, RF beacon tracking system for stereotactic ablative body radiotherapy (SABR) monotherapy for low-risk prostate cancer, kV/MV/CBCT images for routine patient set up and radiation isocenter verification for brain SRS treatment. Those patient positioning technologies have been developed to improve accuracy and precision of the treatment. Those techniques enable clinicians to deliver high doses of radiation directly to the tumor while potentially avoiding healthy surrounding tissues with the increased precision and decreased margin. However, those systems require periodic measurements of specified parameters. QA phantoms take up a significant amount of storage space within a radiation therapy department, and require the medical physicist to set up several different phantoms, which increases the total time required for QA, and reduce the phantom positional reproducibility. The most time-consuming part is to setup the phantom, after that it is just routine data acquisition. With the integrated QA phantom of the current invention, physicists only need to setup the phantom once and followed by the designed QA procedure. A phantom placed at the isocenter should have shifts of less than 1-2 mm dependent what radiation treatment procedure will be done on the particular machine. Previous studies showed the surface imaging systems have demonstrated calibration within 1 mm and 1° which also agree with this current study. Another study evaluated the optical surface monitoring system in respect to the CBCT imaging system which is also comparable to the result showed the accuracy for positioning with differences is less than 1 mm for linear vector displacement and less than 0.5° rotational inaccuracy. The RF beacon tracking system accuracy is comparable to the previous result which evaluated the phantom provided by vendor.

It is very crucial that if the isocenter from each system can be linked so physicists know how far away they are and when we design the treatment we know how much margin is needed to add from image isocenter to the isocenter of monitoring system—ideally it should be the same. Current QA methods can only link the kV to MV and then MV to the localization device. It requires individual calibration for each system. The current invention provides an integrated QA phantom and procedure to quantize the deviation between each localization and positioning system. Demonstrated herein, with integrated QA phantom it is possible to reveal the deviation from each system.

It is essentially to effectively and reliably perform routine QA checks independent from the vendor's method. In this study, for the first time, we developed and evaluated an intergraded phantom for radiographic and non-radiographic localization and positioning systems, as well as dose measurement. On top of the routine QA, the integrated QA phantom of the current invention also can verify the rotation accuracy of optical surface monitoring system and RF beacon tracking systems that is not currently available. With integrated QA phantom it is possible to know the physical distance between each system.

TABLE 1

The distance of isocenter between the calibrated isocenter and the phantom

|  | 270° | 315° | 45° | 90° | 0° |
|---|---|---|---|---|---|
| Vrt (mm) | 0.11 ± 0.14 | 0.23 ± 0.13 | 0.23 ± 0.13 | 0.19 ± 0.15 | 0.22 ± 0.15 |
| Lat (mm) | 0.16 ± 0.11 | 0.16 ± 0.16 | −0.42 ± 0.20 | −0.16 ± 0.23 | 0.14 ± 0.10 |
| Lng(mm) | 0.51 ± 0.10 | 0.01 ± 0.11 | 0.28 ± 0.29 | −0.64 ± 0.30 | 0.27 ± 0.18 |
| Rtn (°) | −0.04 ± 0.11 | −0.04 ± 0.10 | −0.06 ± 0.08 | 0.02 ± 0.08 | 0.08 ± 0.09 |
| Roll (°) | −0.23 ± 0.07 | 0.00 ± 0.08 | −0.13 ± 0.07 | −0.12 ± 0.06 | 0.04 ± 0.10 |
| Pitch (°) | −0.27 ± 0.09 | −0.17 ± 0.07 | 0.01 ± 0.07 | −0.01 ± 0.09 | 0.02 ± 0.10 |

TABLE 2

Comparison between vendor's phantom and S-Phantom

| (n = 10) | optical surface monitoring system (n = 10) | |
|---|---|---|
| Isocenter location | N/A | 0.44 ± 0.08 mm |
| Rotational verification | N/A | <0.3° |
| | RF Tracking (n = 10) | |
| Isocenter location | 1.14 ± 0.31 mm | 1.05 ± 0.20 mm |
| Rotational verification | N/A | <1° |
| | Winston-Lutz (n = 10) | |
| Isocenter location | 0.18 ± 0.05 mm | 0.18 ± 0.06 mm |
| | Total QA Time | |
| | ≈60 min | ≈20 min |

The invention disclosed was designed and evaluated a novel integrated phantom for radiographic and non-radiographic localization and positioning systems for radiotherapy.

With the design the insertable bar, the phantom can also be used for dose measurements without moving the phantom. With this phantom, the variation in measurements are reduced and simplify QA procedures.

Figure 1A:
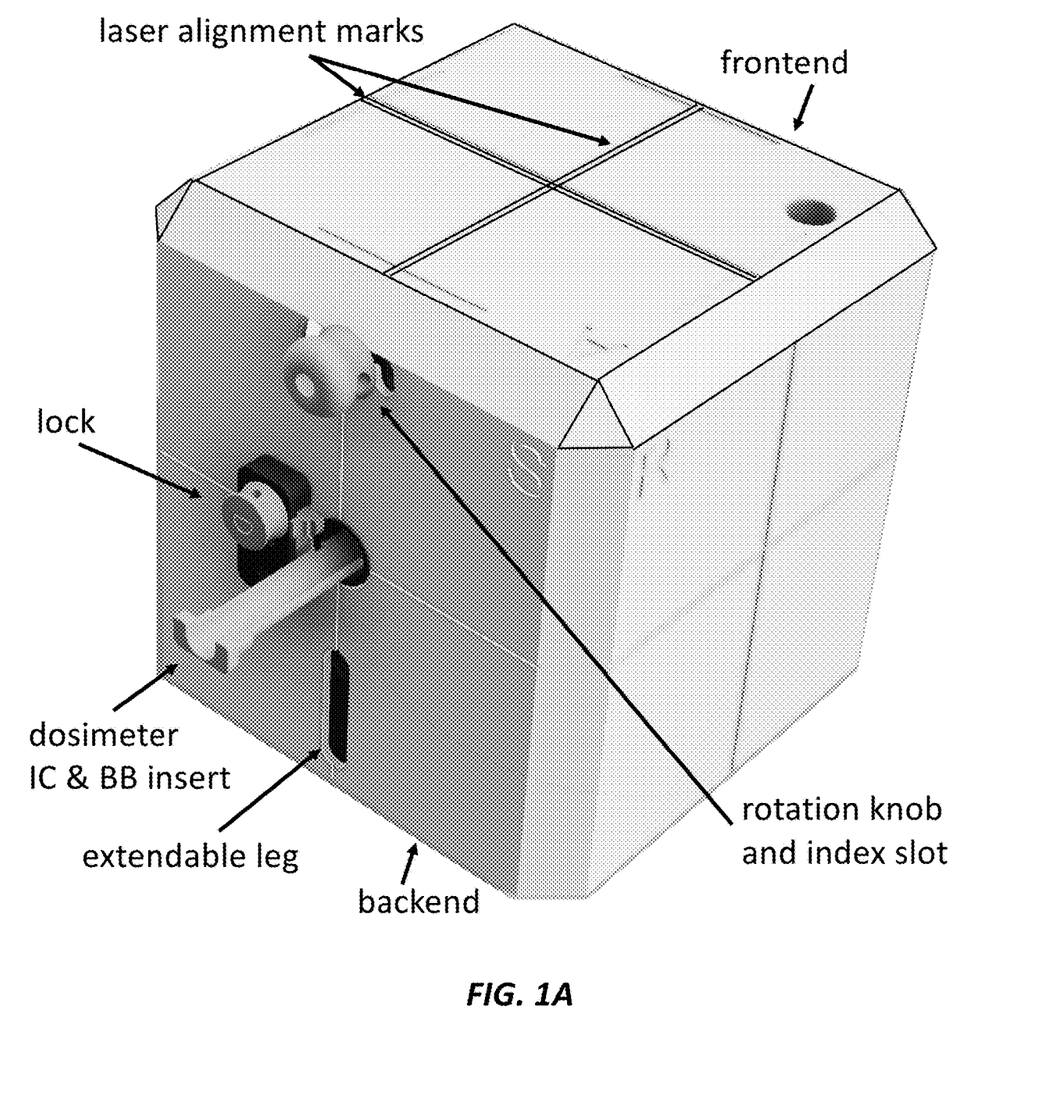
FIGS. 1A-1E show the different views of the integrated phantom. The (FIG. 1A) control levers on the backside and laser alignment marks on at least a topside, (FIGS. 1B-1C) an internal backside view of the phantom controls, (FIG. 1D) an exploded view of the isocenter and BB insert bar, and (FIG. 1E) a perspective view of the integrated phantom front side.
Figure 1B:
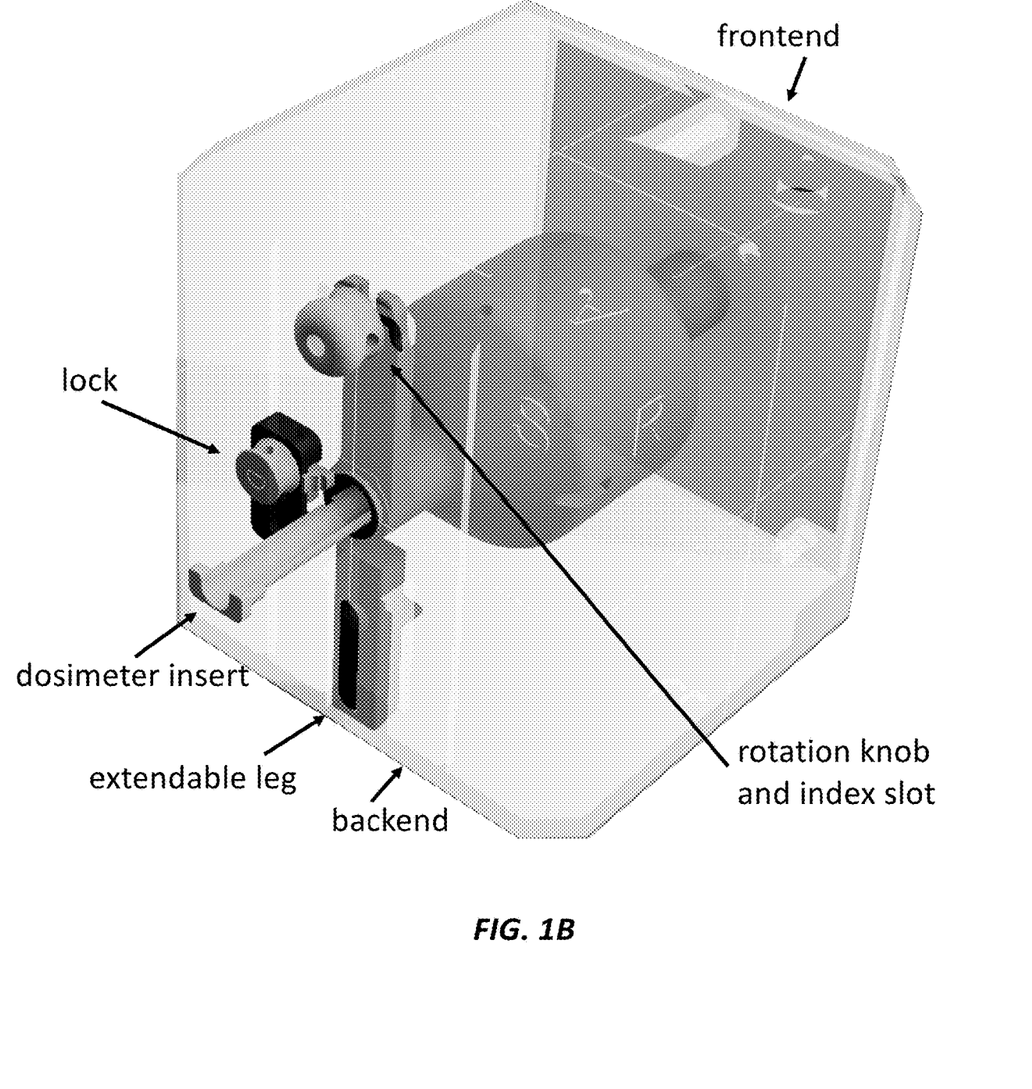
Figure 1C:
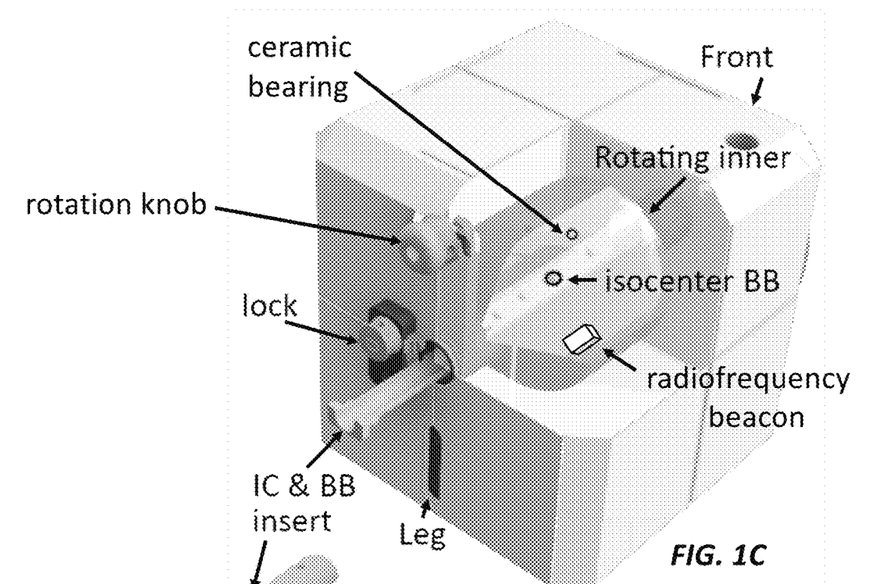
Figures 1D, 1E:
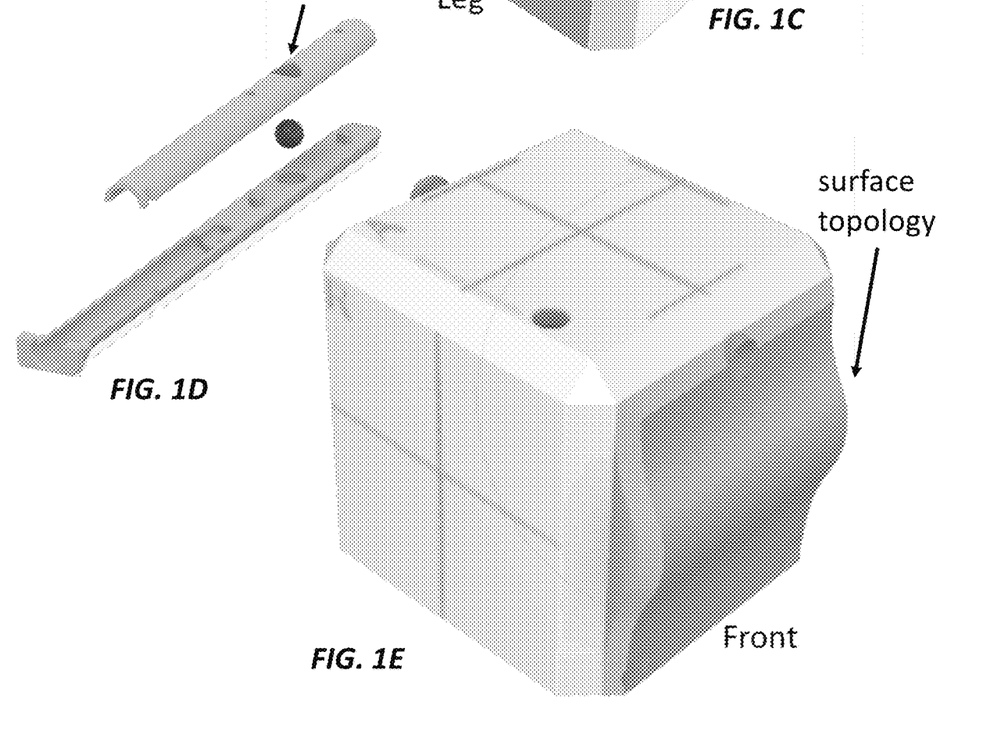
Figure 4B:
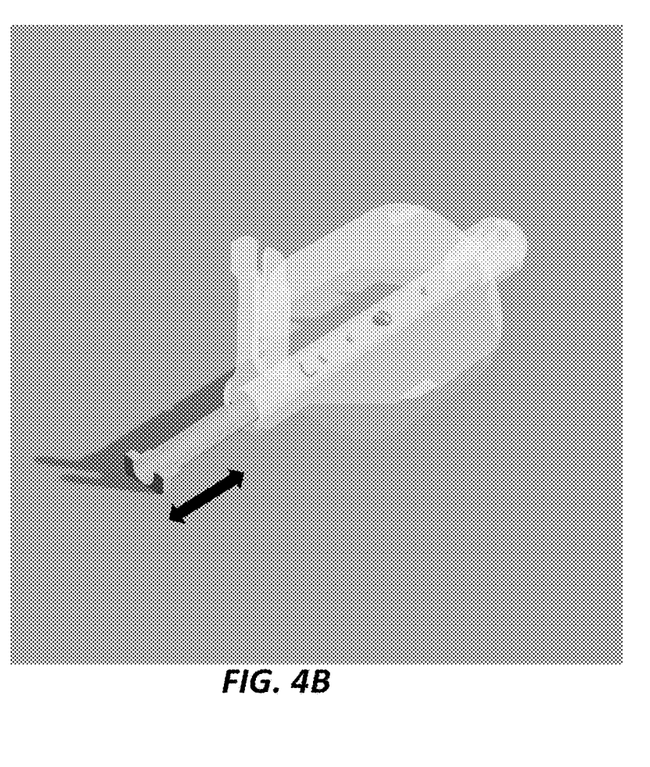

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, the movable insert can switch between the Winston-Lutz test and the dose measurement without moving the phantom itself. A 3.5 cm build-up was designed for the energies of 6 MV and 10 MV. This embodiment of the integrated QA phantom was designed in Fusion 360 CAD software (Autodesk, San Rafael, Calif. USA) and printed using an Ultimaker 2+3D printer (Geldermalsen, The Netherlands). The printing materials used were PLA (polylactic acid) and nylon plastics. The phantom also includes 3 mm diameter alumina ceramic ball bearings (for alignment using CBCT, kV and MV imaging), 2 mm diameter steel ball bearings (for radiation vs light field alignment) and an interchangeable 6 mm diameter central ball bearing with alumina, steel and tungsten options (for Winston-Lutz tests). Alumina ceramic was chosen due to its medium density and high ratio of density to effective-Z. The design was optimized for 3D printing by minimizing overhangs in any single piece. The phantom is constructed of four major component groups, and several smaller mechanical parts. From the outside in, the major parts are the 5-sided outer shell and the front plate which is curved to create a feature for the optical surface imaging system. Inside there is a solid central drum, printed in PLA plastic at a density of 1.1 g/cc. This drum contains 3 ceramic ball bearings and 3 RF-beacons. This central drum is connected to a rocking arm that allows for 10° predefined angle adjustments. This 10° rocking arm allows for verification of rotations reported by the RF-tracking. Inside the drum there is an independent insert which contains the isocenter ball bearing and an ion chamber insert. FIG. 1D shows the insert is provided in 2 parts that mate together; it also slides between two positions, as shown in FIGS. 4A-4B: fully inserted for the ion chamber at isocenter, and a second position, that can be locked in-place, where the ball bearing is at isocenter. The 2 parts construction ensures that the central ball bearing and ion chamber placement can be easily changed or inspected. The main outer shell is 120×120×120 with 2 mm wall thickness and chamfered corners to increase durability. The chamfering, and the rounded front plate also provide surface features for the surface imaging guidance system. FIGS. 1A-1B show a notch-lock mechanisms were designed to lock the central ion chamber insert and the isocenter ball bearing in-place. The extendable leg also allows the user to tilt the phantom 10° predefined degrees, enabling verification of the angles reported by the surface imaging. To ensure the phantom remains stationary an exact bar mount was also designed, as shown in FIGS. 2A-2B. It slides over the two 9 "spaced" diameter pins on the exact bar and is compatible with several systems of this design type. All such variations are considered to be within the scope and spirit of the present invention as defined by the following claims and their legal equivalents.

What is claimed:

1. An integrated localization and dosimetry phantom quality assurance (QA) system for radiotherapy, comprising:
 a) a cubic housing comprising a raised topology feature on an exterior surface of said cubic housing, and at least one laser alignment mark on an exterior surface of said cubic housing that is adjacent and perpendicular to said anterior surface;
 b) at least one extendable leg disposed on a edge of said cubic housing, wherein said at least one extendable leg comprising a retracted state and an extended state, wherein said cubic housing rests on a treatment couch surface when said at least one extendable leg is in said retracted state, wherein when in said extended state said at least one extendable leg is disposed downward from said edge of said cubic housing, wherein said cubic housing rests on said treatment couch surface in a tilted position when said at least one extendable leg is in said deployed state; and
 c) a rotational stage disposed within said cubic housing, wherein said rotational stage comprises at least one radiofrequency beacon, wherein said rotational stage comprises a rotation actuator that is external to said cubic housing, wherein said rotational stage enables verification of a radiofrequency beacon tracking system;

wherein said raised feature enables verification of a radiotherapy optical surface monitoring system, wherein said at least one tilt leg enables a rotational verification of said radiotherapy optical surface monitoring system.

2. The integrated localization and dosimetry phantom system of claim 1, wherein said rotational stage comprises a drum disposed within a center region inside said cubic housing, wherein said at least one radiofrequency beacon for said RF tracking system comprises a distribution of 3 ceramic ball bearings for imaging localization, and a dosimeter for dose measurement.

3. The integrated localization and dosimetry phantom system of claim 2, wherein said drum comprises an independent insertable isocenter ball bearing, wherein said drum comprises at least one dosimeter insert, wherein said at least one dosimeter insert comprises a holder configured to translate between a first position and a second position, wherein said first position comprises said dosimeter at an isocenter position and said second position comprises said ball bearing at said isocenter, wherein said insert comprises a two part construction configured for inspecting said ball bearing and said dosimeter placement.

4. The integrated localization and dosimetry phantom system of claim 1, wherein said raised feature comprises a nonlinear raised feature.

5. The integrated localization and dosimetry phantom system of claim 1, wherein said at least one laser alignment mark comprises a vertical laser alignment mark and a horizontal laser alignment mark.

6. The integrated localization and dosimetry phantom system of claim 1, wherein said rotational stage is disposed for rotational verification of radiofrequency beacon tracking, wherein said at least one radiofrequency beacon is disposed on at least one planar sheet, wherein said at least one planar sheet is separated from another said at least one planar sheet holding another said at least one beacon, wherein said separation of said planar sheets is configured for a Winston-Lutz test.

7. The integrated localization and dosimetry phantom system of claim 1, wherein said rotational stage further comprising an isocenter element, wherein said isocenter element is disposed at an interior isocenter said cubic housing, wherein said at least one radiofrequency beacon is disposed outside a field of radiation directed at said isocenter element, wherein said at least one radiofrequency beacon and said isocenter element enable verification of a QA test selected from the group consisting of a kV radiology imaging test, a MV radiology imaging test, cone beam computed tomography (CBCT) test, and a Winston-Lutz radiology test.

8. The integrated localization and dosimetry phantom system of claim 1, wherein said at least one radiofrequency beacon is disposed outside a radiation field when said the beacons will be outside radiation field for a Wilson-Lutz test.

9. The integrated localization and dosimetry phantom system of claim 1, wherein said cubic housing comprises a 3D printable material.

10. The integrated localization and dosimetry phantom system of claim 1 further comprising an integrated localization and dosimetry phantom positioning bar mount configured to affix to said treatment couch.

* * * * *